US008101211B2

(12) United States Patent
Chiba et al.

(10) Patent No.: US 8,101,211 B2
(45) Date of Patent: Jan. 24, 2012

(54) COMPOSITIONS FOR RETARDING SKIN AGING

(75) Inventors: Katsuyoshi Chiba, Tokyo (JP); Toshiro Sone, Tokyo (JP); Kouji Miyazaki, Tokyo (JP); Tomoko Hanamizu, Tokyo (JP); Fukiko Nishisaka, Tokyo (JP); Sachiko Matsumoto, Tokyo (JP); Ritsuo Aiyama, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 634 days.

(21) Appl. No.: 10/450,181

(22) PCT Filed: Dec. 10, 2001

(86) PCT No.: PCT/JP01/10782
§ 371 (c)(1),
(2), (4) Date: Jun. 10, 2003

(87) PCT Pub. No.: WO02/47656
PCT Pub. Date: Jun. 20, 2002

(65) Prior Publication Data
US 2004/0028643 A1 Feb. 12, 2004

(30) Foreign Application Priority Data

Dec. 15, 2000 (JP) ................................. 2000-381813

(51) Int. Cl.
*A61K 36/00* (2006.01)
(52) U.S. Cl. ........................................ 424/725; 424/401
(58) Field of Classification Search .................. 424/401, 424/195.18, 424, 725
See application file for complete search history.

(56) References Cited

U.S. PATENT DOCUMENTS

| 4,129,644 | A | | 12/1978 | Kalopissis et al. | |
| 4,741,915 | A | * | 5/1988 | Farr et al. ....................... | 426/542 |
| 5,023,175 | A | * | 6/1991 | Hosoya et al. ................. | 435/101 |
| 5,073,545 | A | * | 12/1991 | Arima et al. .................... | 514/27 |
| 5,738,856 | A | * | 4/1998 | Korb et al. ..................... | 424/401 |
| 5,773,004 | A | * | 6/1998 | Takahashi ...................... | 424/774 |
| 5,824,327 | A | * | 10/1998 | Whittemore et al. .......... | 424/401 |
| 5,989,556 | A | * | 11/1999 | Tsai et al. ...................... | 424/741 |
| 6,030,623 | A | * | 2/2000 | Meade ............................ | 424/776 |
| 6,261,565 | B1 | * | 7/2001 | Empie et al. ................... | 424/757 |
| 6,290,993 | B1 | * | 9/2001 | Anderson et al. .............. | 424/725 |
| 6,451,354 | B1 | * | 9/2002 | Hebert et al. .................. | 424/725 |
| 2002/0173472 | A1 | * | 11/2002 | Pezzuto et al. .................. | 514/25 |

FOREIGN PATENT DOCUMENTS

| JP | 51151315 | A | * | 12/1976 |
| JP | 55-87712 | A | | 7/1980 |
| JP | 59-10324 | B2 | | 3/1984 |
| JP | 61-277626 | A | | 12/1986 |
| JP | 1-128933 | A | | 5/1989 |
| JP | 2-11520 | A | | 1/1990 |
| JP | 4-342519 | A | | 11/1992 |
| JP | 05017365 | A | * | 1/1993 |
| JP | 5-310549 | A | * | 11/1993 |
| JP | 05306213 | | * | 11/1993 |
| JP | 5-320024 | A | | 12/1993 |
| JP | 5-331037 | A | | 12/1993 |
| JP | 06009371 | A | * | 1/1994 |
| JP | 6-24937 | A | | 2/1994 |
| JP | 6-80553 | A | | 3/1994 |
| JP | 0797312 | A | * | 4/1995 |
| JP | 7-157420 | A | | 6/1995 |
| JP | 7-277944 | A | | 10/1995 |
| JP | 07258063 | A | * | 10/1995 |
| JP | 8-259431 | A | | 10/1996 |
| JP | 8-283172 | A | | 10/1996 |
| JP | 9-002965 | A | | 1/1997 |
| JP | 9-87136 | A | | 3/1997 |
| JP | 9-87137 | A | | 3/1997 |
| JP | 9-95420 | A | | 4/1997 |
| JP | 09194334 | A | * | 7/1997 |
| JP | 10-046143 | A | | 2/1998 |
| JP | 2000-136123 | A | | 5/2000 |
| JP | 2000-178168 | A | | 6/2000 |
| JP | 2000169381 | A | * | 6/2000 |
| JP | 2000178198 | | * | 6/2000 |
| JP | 2001-233727 | A | | 8/2001 |
| WO | WO 98/43608 | A1 | | 10/1998 |

OTHER PUBLICATIONS

"Hyaluronidase inhibitors for addtion to cosmetics and quasi drugs", Derwent Acc. No. 1994-068304, Jan. 18, 1994, Abstract.*
Nakamura et al. "Cosmetic" JP 05-306213, Nov. 19, 1993, Raw Machine Translation.*
Lin, J. et al. "Studies on Taiwan Folk Medicine, Than-kau-tin (II): Measurement of Active Oxygen Scavenging Activity Using an ESR Technique", 1995, American J. of Chinese Medicine, Vol. XXIII, No. 1, pp. 43-51.*
Katagiri, T. et al, "Cosmetic", JP407097312A, Apr. 11, 1995, Abstract.*
Eijkhoff, P., "Wine in China", 2000, http://www.eykhoff.nl/Wine_in_China_UK.htm, printed on Sep. 10, 2007.*
Okumura, T. et al. "Hair tonic and hair nourishing agent", Jul. 29, 1997, JP 09194334A, abstract.*
Nishida et al. "Antihypertensive agent", Jun. 20, 2000, Derwent Acc. No. 2000-493016, abstract.*

(Continued)

*Primary Examiner* — Gina C Yu
(74) *Attorney, Agent, or Firm* — Holtz, Holtz, Goodman & Chick PC

(57) ABSTRACT

A composition for retarding skin aging which contains an edible herb medicine or medicines round in Taiwan, in particular a plant extract or extracts having melanin formation-unhibiting, elastase-inhibiting, hyaluronidase-inhibiting, active oxygen-eliminating and/or radical-capturing type antioxidant activities, and a medicinally acceptable base and/or additives for external dermal application. The composition is useful in promoting skin whitening effects, maintaining the tension and elasticity of the skin, facilitating skin moistening and providing the skin with anti-inflammatory and/or anti-allergic properties.

3 Claims, No Drawings

OTHER PUBLICATIONS

Hirayama et al., "Production of anticarcinogenic AK-3A and AK-3B from *Mallotus repandus* Muell. obtained by extracting appropriate leaves, bark and wood", Dec. 24, 1976, Derwent Acc. No. 1977-11730Y, Abstract.*

Kawaguchi et al., "Testosterone 5 alpha-reductase inhibitor", Jan. 26, 1993, JP405017365A, Abstract.*

Mitsuyama, S. et al., "Skin External Preparation", JP 05310549 A, Nov. 22, 1993, abstract.*

Kondo, C. et al. "External preparation for skin", JP407258063 A (Oct. 9, 1995), abstract.*

Hayashi, T. et al., "Cell Activator", JP2000-178198, Jun. 27, 2000, machine translation.*

*Fragrance Journal,* vol. 18, No. 6, (1990), pp. 47-52.

*Fragrance Journal,* vol. 18, No. 6, (1990), pp. 53-58.

* cited by examiner

COMPOSITIONS FOR RETARDING SKIN AGING

TECHNICAL FIELD

The present invention relates to a composition for retarding skin aging and, more particularly, to a composition comprising a certain specific herb medicine or medicines selected from among various plant extracts having melanin formation-inhibiting, elastase-inhibiting, hyaluronidase-inhibiting, active oxygen-eliminating and/or radical-capturing type antioxidant activities. The composition, when incorporated in certain preparations, is useful in promoting the so-called whitening effects, namely skin whitening effects, maintaining the tension and elasticity of the skin, facilitating skin moistening and, further, providing the skin with anti-inflammatory and/or anti-allergic properties.

BACKGROUND ART

As for the inhibition of melanin formation, certain whitening agents such as ascorbic acid or derivatives thereof, placenta extracts, kojic acids, glutathion, hydroquinone and a derivative thereof (arbutin), and plant extracts have so far been incorporated in dermatologic preparations for skin whitening for the purpose of preventing such phenomena as sunburn-induced skin darkening or inflammation and pigmentation-due formation of spots and freckles (Fragrance Journal, Vol. 18, No. 6, 1990, pp. 47-58).

Meanwhile, elastase is a protease specifically acting on elastin, which is concerned with the tension and elasticity of the skin. This participates in decreasing the quantity of elastin, leading to particularly grave results among the skin aging phenomena. Further, ultraviolet rays activate elastase, with the results that the skin loses it tension and elasticity. The effect of elastase increases with the advance of age, bringing about the same results. Therefore, if the excessive effect of elastase can be lessened, it will become possible to prevent the skin aging due to ultraviolet rays and/or aging. From such viewpoint, substances having elastase inhibiting activity have been searched for. As a result, it has been demonstrated that extracts from *Schima* species, eucalyptus, and Meniran (*Phylianthus niun*) or Kemiri (*Aleurifis moluccana*), among others are effective for such purposes (JP-A-9-095420, JP-A-9-087137, and JP-A-9-087136).

As for hyaluronidase, its functions in connective tissues are considered to retain water intercellular spaces, form a jelly-like matrix in the tissue to maintain cells, maintain skin lubricity and flexibility, and protect the skin against external forces (mechanical lesions) and bacterial infection. It is said that hyaluronic acid in the skin decreases with aging, with the result that such aging phenomena as fine wrinkles formation and skin roughening. Therefore, it is considered that inhibition of the activity of hyaluronidase, which decomposes such hyaluronic acid, may contribute to the stabilization of skin hyaluronic acid and will be also effective in improving the barrier function of the skin by preventing the same from decreasing. Presumably, this also contribute to stabilization of hyaluronic acid used in preparations for the treatment of arthritis, among others, and further to stabilization of hyaluronic acid in preparations applied to the skin for improving the skin function.

Hyaluronidase is also known as an inflammatory enzyme, and it is known that inhibition of its activity is effective in reducing inflammation and that it suppresses allergy as well. Several substances capable of inhibiting hyaluronidase have been reported. Hyaluronidase inhibiting activity has been confirmed in extracts of peony root, *coptis rhizome* (JP-A-1-128933), ziyu (*Sanguisorba officinalis*), geranium herb (JP-A-2-011520), *Mimusops elengi, Eugenia jambolana, Saraca indica, Mucuna birdwoodiana* or *Millettina nitida* or *dilisiana*, senkakuso (*agrimoniae herba*), and *Machilus thubergii* or *japonica* (JP-A080553), among other herb medicines.

Active oxygen eliminators having SOD activity are widely used in the treatment and/or alleviation, for instance, of various diseases caused by active oxygen ($O_2^-$), for example circulatory disturbance-due diseases (myocardial infarct, cerebral apoplexy, hypertension, menstrual pain, muscle stiffness of shoulder, neuralgia, lumbago, hangover, etc.), adult diseases/internal diseases (cancer, nephritis, hepatitis, diabetes, etc.), cosmetic and skin diseases (spots, freckles, dry/rough skin, cold feeling, constipation, wrinkles, atopic dermatitis, etc.). They can also be used in the fields of foods, food additives, cosmetics, drugs, etc.

More specifically, there are known cosmetics in which various characteristics of SOD are utilized (e.g. JP-B59-010324, JP-A-55-087712) and dermatologic preparation compositions comprising a placenta or liver extract having stable SOD activity (JP-A61-277626). Further known as plant extracts having SOD activity are plant flavonoid-containing extracts of *Cassia nomame, Lycium chinense* or *barbarum, Antemisia capillanes* or scoparia, *Alnus sieboldiana* or firma, *Sophora japonica, Polygonum multiforum, Cassia obtusifolia* or *tora*, sinom nium stem, *Rubia argyi, Acorus gramineus, Rosa laevigata, Taxus cuspidata* (JP-A-8-283172), hibiscus, aloe, rhubarb, osei (*polygonati rhizoma*), bearberry leaf, enmeiso (*plectranthi herba*), gardenia fruit, yobaihi (*nyrice cirtex*), pueraria root, bupleurum root, cnidium rhizome, atractylodes lancea rhizome, mentha leaf, poria sclerotium, glycyrrhiza, peony root, sin'i (*magnoalae flos*), *Saururus chinensis*, Japanese angelica root, cinnamon bark, houttuynia herb, coptis rhizome, moutan bark, gentian, nutgall, swertia herb, geranium herb, ephedra herb, phellodendron bark, almond, dried ginger, jujube, scutellaria root, citrus unshu peel, turmeric, nindo (*lonicerae folium cum caulis*), apricot fruit, rehmannia root, garlic, sage, oregano, rosemary, laurel, celery, thyme, tarragon, onion, nutmeg, mace, clove, Japanese horseradish, savory, basil, red pepper, roasted bean, black tea, green tea, persimmon leaf, coffee, horsetail, henon bamboo, mugwort, low striped bamboo, matrimony vine, *Cyrtomium* species, shiitake mushrooms, ginkgo (JP-A-06-024937), scutellaria root, gingko, *Mucuna birdwoodiana* or *Millettia nitida* or *dillsiana*, sanzasi (*crataegi fructus*), maikaika (*rosae rugosae flos*), saxifrage, Melissa, geranium herb, moutan bark, parsley, tormentil, rakanka (*momordicae fructus*), yashajitsu (fruit of *Alunus firma*), and zikoppi (*lycii cortex*) (JP-A-10-307680).

Referring to antioxidants, sebum is secreted on the human skin to protect the same. When exposed to ultraviolet rays, for instance, this sebum is oxidized to give lipid peroxides, which irritate the skin. These lipid peroxides attack the cell membrane, damaging or adversely affecting the same in various ways, and these damages, in turn, are said to be involved in human skin aging. Therefore, it is considered effective not only in preventing the skin condition from worsening but also in preventing the living body from aging to inhibit the formation of such lipid peroxides by means of antioxidants.

Among specific antioxidants, there have been reported plants extracts such as extracts from birch (*Betula platyphylla*) (JP-A-10-046143) and various plant extracts obtained by extraction, with water or a lower alcohol or an aqueous lower alcohol solution, of at least one plant selected from the group consisting of hibiscus, aloe, rhubarb, osei (*polygonati rhizoma*), bearberry leaf, enmeiso (*plectranthi herba*), yobaihi (*nyricae cirtex*), pueraria root, cnidium rhizome, atractylodes lancea rhizome, mentha leaf, glycyrrhiza, peony root, coix seed, sin'i (*magnoliae flos*), cinnamon bark, houttuynia herb, coptis rhizome, moutan bark, gentian, nutgall, swertia herb, geranium herb, phellodendron bark, dried ginger, scutellaria root, chulling (*poly porus*), garlic, sage, oregano, rosemary, laurel, celery, thyme, tarragon, nutmeg, mace, clove, Japanese horseradish, savory, basil, red pepper, roasted bean, black tea, green tea, persimmon leaf, coffee, horsetail, henon bamboo, mugwort, *Cynostemma* species, low striped bamboo, matrimony vine, *Cyrtomium* species, and shiitake mushrooms (JP-A6-024937).

As regards the melanin formation, however, some dermatologic preparations containing these whitening agents are unsatisfactory in whitening effec, and others are effective in inhibiting melanin formation but still have problems from the safety viewpoint. In many instances, the whitening agents are denatured in the preparations, for instance, hence the desired effects are not obtained. Improvements in this respect have thus been desired.

As regards the elastase activity inhibition, if the excess elastase activity can be inhibited, it may become possible to prevent skin aging. However, the elastase inhibitors so far reported are not fully satisfactory from the viewpoint of stability, effect, and feel upon application.

As for the hyaluronidase activity inhibition, in spite of various investigations in search of cosmetic ingredients having antinflammatory or antiallergic activity, any safe and promising one has not yet been obtained. Thus, substances have been desired which are natural products and have been eaten by men for long and whose safety has thus been established and which have strong hyaluronidase inhibiting activity and further have some other effect on the skin.

The in vivo enzyme superoxide dismutase (SOD) is known as an active oxygen eliminator. However, this is difficult to purify, thermally unstable and readily deactivated, hence it is very expensive. Therefore, the advent of SOD substitutes (substances having SOD-like activity) which show active oxygen eliminating activity, like SOD and are highly stable and can be obtained at low cost has been awaited.

As for the antioxidants so far used, cosmetics and dermatologic preparations containing BHT, BHA and the like tend to cause contact dermatitis and their safety is questionable. On the other hand, gallic acid derivatives and vitamin E species are insufficient in antioxidant activity and thus fail to effectively prevent fat/oil-containing products from becoming rancid. Even if the effect of preventing skin aging due to peroxidation of skin lipids, in particular, is expected of the dermatologic preparations containing them, no satisfactory effects can be obtained.

Further, referring to the whitening effect, the direct inhibitory effect on melanin-synthesizing melanocytes as well as the effect of suppressing the production of melanocyte-stimulating agents (MSH, endotehlin, NO, histamine, PGE2, etc.) released by melanocyte-surrounding cells is an important factor. Therefore, the antinflammatory action inhibiting these stimulators from being released by keratinocytes is also considered to be effective in promoting whitening.

Furthermore, ascorbic acid derivatives and arbutin, which are whitening agents in conventional use, have themselves antioxidant activity, and it Is considered that their active oxygen- and free radical-quenching activity is party involved in the mechanisms of whitening. Therefore, herb extracts having such whitening and antioxidant activities together with antiinflammatory and other activities will be more effective.

However, no investigations have so far been made in search of such herb medicine extracts having such a plurality of activities.

DISCLOSURE OF INVENTION

It is an object of the present invention to provide a composition for retarding skin aging which can promote whitening, allow the skin to retain its tension and elasticity, facilitate skin moistening, and exert antiinflammatory and antiallergic effects on the skin.

In an aspect of the invention, the skin age-retarding composition comprises, together with a base and/or additive medicinally acceptable for external dermal application, one or more plant extracts selected from the group consisting of extracts of Suei-Ding Hsiang (*Ludwigia octovalvis*), Yui-Jen-Sau (*Ansomeles indica*), Ban-Ji-Lien (*Scutellaria rivularis*), Chi-Mu-Sau (*Urena lobata*), Ma-Bien-Sau (*Verbana officinalis*), Tu-Chi-Chi (*Cuscuta australis*), Ma-Ti-Gin (*Dichondra micrantha*), Yeh-Sia-Chu (*Phyllanthus urinaria*), Ku-Chi (*Physalis angulata*), Bai-Hua-Tsai (*Cleome gynandra*), San-Jei-Tsai (*Rorppa indica*), Pien-Di-Gin (*Hydrocotyte formosana*), Samg-Han-Sau (*Vemonia cinerae*), Gin-New-Kou (*Spilanthes acmella*), Mei-Zen-Giau (*Canna indica*), Ma-Ar-Tung (*Ipomoea pes-caprae*), Hua-Shi-Su (*Clerodendrum calamitosum*), Gin-Di-Lo (*Drosera burmanni*), Gin-Hsien-Lien (*Anoectochilus formosanus*), Nan-Ung-Yia-Hua (*Wikstroemia indica*), Bai-YehChi-Ken (*Elaeagnus oldhamii*), Yui-Yeh-Gin-Hua (*Mussaenda parviflora*), Taiwan Ma-Dou-Ling (*Aristolochia mollis*), Huang-Gin-Guei (*Cudrania cochinchinensis* var. *gerontogea*), Chou-Mor-Li (*Clerodendrum phillippinum*), Da-Ching (*Clerodendrum cyrtophyllum*), Bai-Lorng-Chun-Hua (*Clerodendrum paniculataum* var. *albifloraum*), Mu-Chu-Ma (*Boehmeria densiflora*), Ya-Jou (*Sapium sebiferum*), San-Yeh-Pu-Tao (*Tetrastigma dentatum*), Hsia-Yeh-Pu-Tao (*Vitis thunbergit*), Gi-Hua-Mu (*Bauhinia championi*), Gin-Shi-Liu (*Bredia oldhami*), Ha-Sai-Hua (*Staurogyne concinnula*), Shi-Sharng-Bor (*Selaginella doederleinii*), Hu-Ji-Chi (*Lespedeza cuneata*), Ci-Yeh-Suei-Ding-Hsiang (*Ludwigia hyssopifolia*), Wu-Jei (*Sphenomeris chusana*), Tie-Hsien-Jei (*Adiantum flabellulatum*) Gi-Yien-Sau (*Kummerowia striata*), Hai-Chou-Chung-San (*Clerodendrum trichotumum*), Huang-Ging (*Vitex negundo*), Hsien-Fong-Sau (*Bidens pilosa* var. *minor*, Su-Chi-Sau (*Gnaphalium Affine*), Tsu-Bei-Sau (*Emilia sonchifolia*), Harn-Hsiu-Sau (*Mimosa pudica*), Zu-Chi-Sau (*Euphorbia hirta*), Cher-Chien-Sau (*Plantago formosana*), Bai-Hua-Tung (*Plumbago zeylanica*), Ding-Di-Wu-Gong (*Torenia concolor* var. *formosana*, Da-Gia-Sau (*Euphorbia formosana*), Gi-Yeh-Tsu-Hua-Di-Ding (*Viola phillippica*), Taiwan Her-Shou-Wu (*Polygonum multiflorum* var. *hypoleucum*), New-Zu-Zong (*Ficus erecta* var. *beecheyana*), Bi-Yeh-Dung-Lorng-Sau (*Kalanchoe spathulata*), Karng-Hsiang-Tung (*Mallotus repandus*), Taiwan Kou-Tung (*Uncaria hirsuta*), Lo-Chi-Yien-Fu-Mu (*Rhus semialata* var. *roxburghiana*), Gin-Gien-Sau (*Rubia lanceolata*), Horng-Hua-Su-Wei-Sau (*Salvia coccinea*), Tu-Chi-Tsai (*Ixeris chinensis*), Dau-Sharng-Sau (*Ixeris laevigata* var *oldhami*), Ku-Larm-Pam (*Clerodendrum inerme*), Du-Horng-Hua (*Callicarpa formosana*), Yeh-Hu (*Aeginetia indica*), Torng-Chuei-Yui-Di-Sau (*Pratia nummularia*), and San-Yeh-Wu-Gia (*Acanthopanax trifoliatus*).

In another aspect of the invention, the skin age-retarding composition comprises, together with a base and/or additive medicinally acceptable for external dermal application, one or more plant extracts having, in particular, melanin formation-inhibiting activity as the aging retarding effect as selected from the group consisting of extracts of Yui-Jen-Sau (*Anisomeles indica*), Chi-Mu-Sau (*Urena lobata*), Tu-Chi-Chi (*Cuscuta australis*), Ma-Ti-Gin (*Dichondra micrantha*), KuChi (*Physalis angulata*), Bai-Hua-Tsai (*Cleome gynandra*), San-Jei-Tsai (*Rorippa indica*), Pien-Di-Gin (*Hydrocotyfe formosana*), Gin-New-Kou (*Spilanthes acmella*), Mei-Zen-Giau (*Canna indica*), Gin-Hsien-Lien (*Anoectochilus formosanus*), Nan-Ling-Yia-Hua (*Wikstroemia indica*), Taiwan Ma-Dou-Ling (*Anstolochia mollis*), HuangGin-Guei (*Cudrania cochinchinensis* var. *gerontogea*), Da-Ching (*Clerodendrum cyrtophyllum*), Gi-Hua-Mu (*Bauhinia championi*), Shi-Sharng-Bor (*Selaginella doededteinil*), Hu-Ji-Chi (*Lespedeza cuneata*), Ci-Yeh-Suei-Ding-Hsiang (*Ludwigia hyssopifolia*), Hsien-Fong-Sau (*Bidens pilosa* var. *minor*), Tsu-Bei-Sau (*Emilia soncritoiia*), Cner-Ch-iei-Sau (*Plantago formosana*), Bai-Hua-Tung (*Plumbago zeylanica*), Ding-Di-Wu-Gong (*Torenia concolor* var. *formosona*), Gi-Yeh-Tsu-Hua-Di-Ding (*Viola phillippica*), New-Zu-Zong (*Ficus eecta* var. *beecheyana*), Bi-Yeh-Dung-Lomg-Sau (*Kalanchoe spathulata*), Gin-Gien-Sau (*Rubia lanceolata*), and Horng-Hua-Su-Wei-Sau (*Salvia coccinea*).

In a further aspect of the invention, the skin age-retarding composition comprises, together with a base and/or additive medicinally acceptable for external dermal application, one or more plant extracts having elastase-inhibiting activity as the aging retarding effect as selected from the group consisting of extracts of YehSia-Chu (*Phyllanthus urinaria*), Nan-Ling-Yia-Hua (*Wikstroemia indica*), Huang-Gin-Guei (*Cudrania cochinchinensis* var. *gerontogea*), Mu-Chu-Ma (*Boehmeria densiflora*), San-YehPu-Tao (*Tetrastigma dentatum*), Hsia-YehPu-Tao (*vitis thunbergit*), Gi-Hua-Mu (*Bauhinia championi*), Gin-Shi-Liu (*Bredia oldhami*), Hu-Ji-Chi (*Lespedeza cuneata*), Ci-YehSuei-Ding-Hsiang (*Ludwigia hyssopifolia*), Tie-Hsien-Jei (*Adiantum filabellulatum*), Harn-Hsiu-Sau (*Mimosa pudica*), Bai-Hua-Tung (P/umbago zeylanica), Ding-Di-Wu-Gong (*Torenia concolor* var. *formosona*), Taiwan Her-Shou-Wu (*Polygonum mulfiflorum* var. *hypoleucum*), Taiwan Kou-Tung (*Uncaria hirsuta*), and Lo-Chi-Yien-Fu-Mu (*Rhus semialata* var. *roxburghiana*).

In a still further aspect of the invention, the skin age-retarding composition comprises, together with a base and/or additive medicinally acceptable for external dermal application, one or more plant extracts having hyaluronidase-inhibiting activity as the aging retarding effect as selected from the group consisting of extracts of Huang-Gin-Guei (*Cudrania cochinchinensis* var. *gerontogea*), Ilsia-YehPuTao (*Vitis thunbergii*), and Gi-Hua-Mu (*Bauhinia championi*).

In a still further aspect of the invention, the skin age-retarding composition comprises, together with a base and/or additive medicinally acceptable for external dermal application, one or more plant extracts having active oxygen eliminating activity as the aging retarding effect as selected from the group consisting of extracts of Suei-Ding Hsiang (*Ludwigia octovalvis*), Yui-Jen-Sau (*Anisomeles indica*), BanJi-Uen (*Scutellana rivularis*), Ma-Bien-Sau (*Verbana officinalis*), Tu-Chi-Chi (*Cuscuta australis*), YehSia-Chu (*Phyllanthus urinaria*), Ku-Chi (*Physalis angulata*), Bai-Hua-Tsai (*Cleome gynandra*), SamgHan-Sau (*Vemonia cinerae*), Mei-Zen-Giau (*Canna indica*), Ma-An-Tung (Ipomoea pes-caprae), Hua-ShiSu (*Clerodendrum calamitosum*), Gin-Di-Lo (*Drosera burmanni*), Nan-Ling-Yia-Hua (*Wikstroemia indica*), Bai-Yeh-Chi-Ken (*Elaeagnus oldhamit*), Yui-Yeh-Gin-Hua (*Mussaenda parvfflora*), Huang-Gin-Guei (*Cudrania cochinchinensis* var. *gerontogea*), Chou-Mor-U (*Clerodendrum phillippinum*), Da-Ching (*Clerodendrum cyrtophyllum*), Bai-LomgChun-Hua (*Clerodendrum paniculataum* var. *albifloraum*), Mu-Chu-Ma (*Boehmenia densiflora*), Ya-Jou (*Sapium sebiferum*), San-YehPu-Tao (*Tetrastigma dentatum*), Hsia-YehPu-Tao (*Vitis thunbefgit*), Gi-Hua-Mu (*Bauhinia championi*), Gin-Shi-Liu (*Bredia oldhami*), Ha-Sai-Hua (*Staurogyne concinnula*), Hu-Ji-Chi (*Lespedeza cuneata*), CiYeh-Suei-DingHsiang (*Ludwigia hyssopifolia*), Tie-Hsien-Jei (*Adiantum flabellulatum*), Hai-Chou-Chung-San (*Clerodendrum trichotumum*), Huang-Ging (*Vitex negundo*), Su-Chi-Sau (*Gnaphalium affine*), Ham-Hsiu-Sau (*Mimosa pudica*), Zu-Chi-Sau (*Euphorbia hirta*), Ding-Di-Wu-Gong (*Torenia concolor* var. *formosona*), Da-Gia-Sau (*Euphorbia formosana*), Taiwan Her-Shou-Wu (*Polygonum multiflorum* var. *hypoleucum*), Kamg-Hsiang-Tung (*Mallotus repandus*), Taiwan Kou-Tung (*Uncaria hirsuta*), Lo-ChiYien-Fu-Mu (*Rhus semialata* var. *roxburghiana*), Cher-Chien-Sau (*Plantago formosana*), Gin-Gien-Sau (*Rubia lanceolata*), Tu-Chi-Tsai (*Ixeris chinensis*), Dau-Shamg-Sau (*Ixeris laevigata* var. *oldhami*), KuLam-Pam (*Clerodendrum inerne*), Du-Homg-Hua (*Callicarpa formosana*), Yeh-Hu (*Aeginetia indica*), Tomg-Chuei-Yui-Di-Sau (*Pratia nummularia*), and San-Yeh-WuGia (*Acanthopanax trifoliatus*).

In a still further aspect of the invention, the skin age-retarding composition comprises, together with a base and/or additive medicinally acceptable for external dermal application, one or more plant extracts having antioxidant activity as the aging retarding effect as selected from the group consisting of extracts of SueiDing Hsiang (*Ludwigia octovalvis*), Yui-Jen-Sau (*Anisomeles indica*), Ban-Ji-Lien (*Scutellaria rivularis*), Ma-Bien-Sau (*Verbana officinalis*), Yeh-Sia-Chu (*Phyllanthus urinania*), Samg-Han-Sau (*Vemonia cinerae*), Ma-An-Tung (*Ipomoea pes-caprae*), Gin-Di-Lo (*Drosera burmanni*), Nan-Ling-Yia-Hua (*Wikstroemia indica*), Bai-Yeh-Chi-Ken (*Elaeagnus cochinchinensis* var. *gerontogea*), Da-Ching (*Clerodendrum cyrtophyilum*), Mu-Chu-Ma (*Boehmeria densiflora*), Ya-Jou (*Sepium sebiferum*), San-YehPuTao (*Tetrastigma dentatum*), Hsia-Yeh-Pu-Tao (*Vitis thunbergit*), Gi-Hua-Mu (*Bauhinia championm*), Gin-Shi-Liu (*Bredia oldhami*), Ha-Sai-Hua (*Staurogyne concinnula*), Hu-Ji-Chi (*Lespedeza cuneata*), Ci-Yeh-Suei-Ding-Hsiang (*Ludwigia hyssopifolia*), WuJei (*Sphenomenis chusana*), Tie-Hsien-Jei (*Adiantum flabellulatum*), Gi-Yien-Sau (*Kummerowia striata*), Hai-Chou-Chung-San (*Clerodendrum trichotumum*), Huang-Ging (*Vitex negundo*), Zu-Chi-Sau (*Euphorbia hirta*), Ding-Di-WuGong (*Torenia concolor* var. *fommosona*), Da-Gia-Sau (*Euphorbia formosana*), Taiwan Her-Shou-Wu (*Polygonum multiflorum* var. *hypoleucum*), New-Zu-Zong (*Ficus erecta* var. *beecheyana*), Kamg-Hsiang-Tung (*Mallotus repandus*), Taiwan Kou-Tung (*Uncaria hirsuta*), and Lo-Chi-Yien-Fu-Mu (*Rhus semialata* var. *roxburghiana*).

The present invention also provides a cosmetic composition and a dermatologic preparation each containing the skin age-retarding composition mentioned above.

The medicinal herbs to be used in accordance with the invention respectively have the common names and scientific names listed below in Table 1. Various parts (whole herb, flower, caput, floral spike, female floral spike, fruit spike, corpus glandulae, leaf, branch, leaf-bearing branch, rhizome, velamen, root, seed, etc.) of each plant may be extracted either as such or after grinding to give extracts ready for use.

TABLE 1

| No. | Name of herb | Botanical name |
| --- | --- | --- |
| 1 | Suei-Ding Hsiang | *Ludwigia octovalvis* |
| 2 | Yui-Jen-Sau | *Anisomeles indica* |

TABLE 1-continued

| No. | Name of herb | Botanical name |
|---|---|---|
| 3 | Ban-Ji-Lien | *Scutellaria rivularis* |
| 4 | Ban-Bien-Lien | *Lobelia chinensis* |
| 5 | Chi-Mu-Sau | *Urena lobata* |
| 6 | Ma-Bien-Sau | *Verbana officinalis* |
| 7 | Tu-Chi-Chi | *Cuscuta australis* |
| 8 | Ma-Ti-Gin | *Dichondra micrantha* |
| 9 | Yeh-Sia-Chu | *Phyllanthus urinaria* |
| 10 | Ku-Chi | *Physalis angulata* |
| 11 | Bai-Hua-Tsai | *Cleome gynandra* |
| 12 | San-Jei-Tsai | *Rorippa indica* |
| 13 | Pien-Di-Gin | *Hydrocotyle formosana* |
| 14 | Sarng-Han-Sau | *Vernonia cinerae* |
| 15 | Gin-New-Kou | *Spilanthes acmella* |
| 16 | Mei-Zen-Giau | *Canna indica* |
| 17 | Ma-An-Tung | *Ipomoea pes-caprae* |
| 18 | Hua-Shi-Su | *Clerodendrum calamitosum* |
| 19 | Gin-Di-Lo | *Drosera burmanni* |
| 20 | Gin-Hsien-Lien | *Anoectochilus formosanus* |
| 21 | Nan-Ling-Yia-Hua | *Wikstroemia indica* |
| 22 | Bai-Yeh-Chi-Ken | *Elaeagnus oldhamii* |
| 23 | Yui-Yeh-Gin-Hua | *Mussaenda parviflora* |
| 24 | Hsien-Sau | *Mesona procumbens* |
| 25 | Taiwan Ma-Dou-Ling | *Aristolochia mollis* |
| 26 | Shi-Chung-Pu | *Acorus gramineus* |
| 27 | Huang-Gin-Guei | *Cudrania cochinchinensis* var. *gerontogea* |
| 28 | Chou-Mor-Li | *Clerodendrum phillippinum* |
| 29 | Da-Ching | *Clerodendrum cyrtophyllum* |
| 30 | Bai-Lorng-Chun-Hua | *Clerodendrum paniculataum* var. *albifloraum* |
| 31 | Mu-Chu-Ma | *Boehmeria densiflora* |
| 32 | Ya-Jou | *Sapium sebiferum* |
| 33 | San-Yeh-Pu-Tao | *Tetrastigma dentatum* |
| 34 | Hsia-Yeh-Pu-Tao | *Vitis thunbergii* |
| 35 | Gi-Hua-Mu | *Bauhinia championi* |
| 36 | Gin-Shi-Liu | *Bredia oldhami* |
| 37 | Ha-Sai-Hua | *Staurogyne concinnula* |
| 38 | Shi-Sharng-Bor | *Selaginella doederleinii* |
| 39 | Hu-Ji-Chi | *Lespedeza cuneata* |
| 40 | Ci-Yeh-Suei-Ding-Hsiang | *Ludwigia hyssopifolia* |
| 41 | Chein-Gin-Tung | *Stephania japonica* |
| 42 | Wu-Jei | *Sphenomeris chusana* |
| 43 | Tie-Hsien-Jei | *Adiantum flabellulatum* |
| 44 | San-Hsiang | *Hyptis suaveolens* |
| 45 | Gi-Yien-Sau | *Kummerowia striata* |
| 46 | Hai-Chou-Chung-San | *Clerodendrum trichotumum* |
| 47 | Huang-Ging | *Vitex negundo* |
| 48 | Sarng-Er | *Xanthium strumarium* var. *japonica* |
| 49 | Hsien-Fong-Sau | *Bidens pilosa* var. *minor* |
| 50 | Su-Chi-Sau | *Gnaphalium affine* |
| 51 | Tsu-Bei-Sau | *Emilia sonchifolia* |
| 52 | Harn-Hsiu-Sau | *Mimosa pudica* |
| 53 | Zu-Chi-Sau | *Euphorbia hirta* |
| 54 | Cher-Chien-Sau | *Ptantago formosana* |
| 55 | Dau-Di-Ling | *Cardiospermum halicacabum* |
| 56 | Bai-Hua-Tung | *Plumbago zeylanica* |
| 57 | Ding-Di-Wu-Gong | *Torenia concolor* var. *formosona* |
| 58 | Da-Gia-Sau | *Euphorbia formosana* |
| 59 | Gi-Yeh-Tsu-Hua-Di-Ding | *Viola phillippica* |
| 60 | Taiwan Her-Shou-Wu | *Polygonum multifloru* var. *hypoleucum* |
| 61 | New-Zu-Zong | *Ficus erecta* var. *beecheyana* |
| 62 | Bi-Yeh-Dung-Lorng-Sau | *Kalanchoe spathulata* |
| 63 | Karng-Hsiang-Tung | *Mallotus repandus* |
| 64 | Taiwan Kou-Tung | *Uncaria hirsute* |
| 65 | Lo-Chi-Yien-Fu-Mu | *Rhus semialata* var. *roxburghiana* |
| 66 | Gin-Gien-Sau | *Rubia lanceolata* |
| 67 | Horng-Hua-Su-Wei-Sau | *Salvia coccinea* |
| 68 | Tu-Chi-Tsai | *Ixeris chinensis* |
| 69 | Dau-Sharng-Sau | *Ixeris laevigata* var. *oldhami* |
| 70 | Ku-Larn-Parn | *Clerodendrum inerme* |
| 71 | Tou-Hua-Hsiang-Ku-Sau | *Hyptis rhomboids* |
| 72 | Du-Horng-Hua | *Callicarpa formosana* |
| 73 | Yeh-Hu | *Aeginetia indica* |
| 74 | Torng-Chuei-Yui-Di-Sau | *Pratia nummularia* |
| 75 | San-Yeh-Wu-Gia | *Acanthopanax trifoliatus* |

The method of producing such medicinal herb extracts is not particularly restricted but may be any of the methods in conventional use. The following method, for example, may be preferably employed. Thus, any of the starting herb materials mentioned above is finely ground, 5 to 10 weights of an extracting solvent (water, alcohol or organic solvent, or mixture thereof) is added, the mixture is allowed to stand at room temperature for at least one week and then filtered, the filtrate is lyophilized, and the lyophilization product is used as a medicinal herb extract. Alternatively, an extracting solvent (water or organic solvent) is added to the herb material and, after a certain period of digestion or heating at the refluxing temperature of the solvent, the mixture is filtered, and the filtrate is concentrated to dryness.

Usable as specific extracting solvents are aqueous solvents (e.g. water, acidic or basic aqueous solvents, etc.), alcohols (e.g. lower alcohol such as methanol, absolute ethanol, ethanol, or polyhydric alcohols such as propylene glycol, 1,3-butylene glycol, etc.), ketones such as acetone, diethyl ether, dioxane, acetonitrile, esters such as ethyl acetate, and organic solvents such as xylene, benzene and chloroform. These may be used either singly or in the form of a mixture of two or more. In particular, water, methanol, ethanol, and 50% ethanol are preferred. Two or more solvent extracts may be used in combination.

In the practice of the invention, the plant extract(s) mentioned above may be used as such or may be admixed with per se known bases or additives medicinally acceptable for dermal application, including, as cosmetics components, for instance, water, alcohols, oleaginous substances, surfactants, preservatives, perfumes, colorants, humectants, thickening agents, water-soluble polymers, antioxidants, chelating agents, pH adjusting agents, foaming agents, (pigments, ultraviolet absorbing/scattering agents, powders), vitamins, amino acids, antimicrobial agents, algae extracts, various drugs, additives, and so forth.

More specifically, the oleaginous substances include vegetable oils and fats such as macadamia nut oil, castor oil, olive oil, cacao oil, tsubaki oil, coconut oil, Japan wax, jojoba oil, grape seed oil, and avocado oil, animal oils and fats such as mink oil and yolk oil, waxes such as beeswax, spermaceti, lanolin, carnauba wax, and candelilla wax, hydrocarbons such as liquid paraffin, squalane, microcrystalline wax, ceresin wax, paraffin wax, and Vaseline, natural or synthetic fatty acids such as capric acid, myristic acid, palmitic acid, stearic acid, behenic acid, lanolin fatty acids, linolic acid, linolenic acid, lauric acid, myristic acid, oleic acid, and isostearic acid, natural and synthetic higher alcohols such as cetanol, stearyl alcohol, hexyldecanol, octyldodecanol, lauryl alcohol, capryl alcohol, myristyl alcohol, cetyl alcohol, cholesterol, and phytosterol, and esters such as isopropyl myristate, isopropyl palmitate, octyldodecyl myristate, octyldodecyl oleate, and cholesterol oleate, among others.

Examples of the above-mentioned surfactants are nonionic surfactants such as sorbitan monolaurate, sorbitan monoplamitate, sorbitan sesquioleate, sorbitan trioleate, polyoxyethylenesorbitan monolaurate, polyoxyethylenesorbitan monostearate, polyethylene glycol monooleate, polyethylene glycol alkylates, polyoxyethylene alkyl ethers, polyglycol diethers, lauroyldiethanolamide, fatty acid isopropanolamides, maltitol hydroxyfatty acid ethers, alkylated polysaccharides, alkyl glucosides, and sugar esters; nonionic surfactants such as lipophilic glycerol monostearate, self-emulsificable glycerol monostearate, polyglycerol monostearate, polyglycerol alkylates, sorbitan monooleate, polyethylene glycol monostearate, polyoxyethylenesorbitan monooleate, polyoxyethylene cetyl ether, polyoxyethyienateu sterol, polyoxyethylenated lanolin, polyoxyethylenated beeswax, and polyoxyethylenated hardened castor oil; anionic surfactants such as sodium stearate, potassium palmitate, sodium cetyl sulfate, sodium lauryl phosphate, palmitic acid triethanolamide, sodium polyoxyethylenelauryl phosphate, sodium N-acylglutamate, sodium palmitate, sodium laurate, sodium lauryl, potassium lauryl sulfate, alkyl sulfate triethanolamine ethers, Turkey red oil, linear dodecylbenzenesulfuric acid, polyoxyethylene-hardened castor oil maleic acid, and acylmethyltaurine; cationic surfactants such as stearyidimethylbenzylammonium chloride, stearyltrimethylammonium chloride, stearyltrimethylammonium chlrodie, benzalkonium chloride, and laurylamine oxide; and amphoteric surfactants such as alkylaminoethylglycine hydrochloride solutions, and lecithin.

Examples of the above preservatives are benzoic acid salts, salicylic acid salts, sorbic acid salts, dehydroacetic acid salts, parahydroxybenzoic acid esters, 2,4,4'-tri-chloro-2'-hydroxydiphenyl ether, 3,4,4'-trichlorocarbanilide, benzalkonium chloride, hinokitiol, resorcinol, and ethanol.

The above humectants include polyhydric alcohols such as glycerol, erythritol, xylitol, maltitol glycerol, propylene glycol, 1,3-butylene glycol, sorbitol, polyglycerol, polyethylene glycol, dipropylene glycol, 1,2-pentanediol, and isoprene glycol; NMF components such as amino acids, sodium lactate, and sodium pyrrolidonecarboxylate; water-soluble polymer substances such as xyloglucan, quince seeds, carrageenan, pectin, mannan, curdlan, galactan, dermatan sulfate, glycogen, keratan sulfate, chondroitin, mucoitin sulfate, keratosulfate, locust bean gum, succinoglucan, charonic acid, hyaluronic acid, heparan sulfate, sodium hyaluronate, collagen, mucopolysaccharides, and chondroitin sulfate; silicones such as dimethylpolysiloxane and methylphenylsiloxane; and culture supernatants such as of lactic acid bacteria/bifidus bacilli, among others.

The above thickeners include, among others, natural polymer substances such as sodium alginate, xanthan gum, aluminum silicate, marmelo seed extracts, gum arabic, hydroxyethyl-guar gum, carboxymethyl-guar gum, guar gum, dextran, tragacanth gum, starch, chitin, chitosan, carboxymethylchitin, and agar; semisynthetic polymer substances such as cellulose, hydroxypropylcellulose, methylhydroxypropylcellulose, methylcellulose, carboxymethylcellulose, hydroxyethylcellulose, soluble starch, and cationized cellulose; and synthetic polymer substances such as carboxyvinyl polymers, polyvinyl alcohol, polyvinylpyrrolidone, and vinyl alcohol-vinyl acetate copolymers.

The above antioxidants include, among others, dibutylhydoxytoluene, butylhydroxyanisole, propyi gaiiate, and ascorbic acid; the chelating agents include, among others, disodium edetate, ethylenediaminetetraacetic acid salts, pyrophosphoric acid salts, hexametaphosphoric acid salts, citric acid, tartaric acid, and gluconic acid; the pH adjusting agents include, among others, sodium hydroxide, triethanolamine, citric acid, sodium citrate, boric acid, borax, and potassium hydrogen phosphate.

The above ultraviolet absorbing/scattering agents include, among others, paraaminobenzoic acid type ultraviolet absorbers, anthranilic acid type ultraviolet absorbers, salicylic acid type ultraviolet absorbers, cinnamic acid type ultraviolet absorbers, benzophenone type ultraviolet absorbers, sugar type ultraviolet absorbers, 3-(4'-methylbenzylidene)-d-camphor, 3-benzylidene-d, I-camphor, urocanic acid, ethyl urocanate, 2-phenyl-5-methylbenzoxazole, 2,2'-hydroxy-5-methylphenylbenzotriazole, 2-(2'-hydroxy-5'-t-octylphenyl) benzotriazole, 2-(2'-hydroxy-5'-methylphenyl)benzotriazole, dibenzalazine, dianisoylmethane, 4-methoxy-4'-t-butylbenzophenone, 5-(3,3-dimethyl-2-norbornylidene)-3-pentan-2-one, 2-hydroxy-4-methoxybenzophenone, octyidiemthyl paraaminobenzoate, ethylhexyl paramethoxycinnamate, titanium oxide, kaolin, and talc.

The above vitamins include, among others, vitamin A and derivative thereof, vitamin B species such as vitamin $B_6$ hydrochloride, vitamin $B_6$ tripalmitate, vitamin $B_6$ dioctanoate, vitamin $B_2$ and derivatives thereof, vitamin $B_{12}$, vitamin $B_{15}$ and derivatives thereof, ascorbic acid, ascorbic acid sulfate and salts thereof, ascorbic acid phosphate and salts thereof, ascorbic acid dipalmitates, ascorbic acid glucosides, acylascorbic acid glucosides, vitamin E species such as α-tocopherol, β-tocopherol, γ-tocopherol, and vitamin E acetate, vitamin D species, vitamin H, pantothenic acid, pantethine, vitamin F, vitamin K, vitamin P, vitamin U, carnitine, ferulic acid, γ-oryzanol, α-lipoic acid, orotic acid and derivatives thereof.

The above amino acids include glycine, alanine, valine, leucine, isoleucine, serine, threonine, phenylalanine, tyrosine, asparagine, glutamine, taurine, tryptophan, cystine, cysteine, methionine, proline, hydroxyproline, aspartic acid, glutamic acid, arginine, histidine, lysine, and derivatives thereof.

The above antimicrobial agents include benzoic acid, salicylic acid, parahydroxybenzoic acid alkyl esters, and hexchlorophene, among others.

The above algae extracts include extracts from brown algae, red algae, green algae, blue algae and so on. More specific examples are extracts from tangle, Japanese tangle, hijiki, agar-agar, coralline, *Palmara*, carrageen moss, laver, sea lettuce, holey sea lettuce, *Ascophyllum*, wrack mozuku, Okinawa mozuku, *Himantaria*, etc.

Specific examples of the various drugs mentioned above are nictlnamiide, benzyl nicotinate, γ-oryzanol, allantoin, glycyrrhizic acid (salts), glycyrrhetic acid and derivatives thereof, hinokitiol, bisabolol, eucalyptone, thymol, inositol, saponins such as psychosaponin, carrot saponin, loofah saponin and soapberry saponin, pantothenyl ethyl ether, ethynylestradiol, tranexamic acid, arbutin, capharanthine, and placenta extract.

In the practice of the invention, the level of incorporation of the medicinal herb extract is not particularly restricted but may be adequately selected according to the intensity ($IC_{50}$ value) of the activity of the extract and the preparation form, for instance. Preferably, the level of incorporation of the medicinal herb extract is selected within the range of 0.0001-30 wt %, more preferably 0.001-10 wt %, on the extract solid basis, relative to the whole amount of the skin age-retarding composition.

The cosmetics, dermatologic preparations, quasi drugs and so forth, which contain the skin age-retarding composition of the invention, can be produced in the conventional manner. They may have various forms, for example, basic cosmetic forms such as skin lotions, milky lotions, moisturizing creams, deansing creams, massage creams, facial cleansing creams, packs, and essence, hair care products such as shampoos and rinses, bath products such as bath salt compositions, makeup cosmetics such as foundations, and special cosmetics such as anti-suntan compositions.

BEST MODES FOR CARRYING OUT THE INVENTION

The following test examples and working examples illustrate the invention in further detail. They are, however, by no means limitative of the scope of the invention.

TEST EXAMPLE 1

Preparation of Medicinal Herb Extracts (Nan-Ling-Yia-Hua)

To 282.3 g of Nan-Ling-Yia-Hua was added 1.8 L of 100% methanol, and extraction was effected at room temperature for 1 week, followed by filtration. The filtrate obtained was evaporated to dryness. The dry weight was 21.49 g (yield 7.6%).

For the medicinal herbs listed in Table 1, 1 to 10 L of 100% methanol was added to about 300 g of each bulk herb medicine, and extraction was effected in the same manner to give an extract. The following Table 2 shows yields of respective extracts in 100% methanol. Also shown in Table 2 are the pH values found when 0.5% solutions were prepared from the dried products, the states of dissolution and the colors as well as the absorbance values (As) at 312 nm in 50% thanol solutions at a solid matter concentration of 0.5%.

TABLE 2

| No. | Herb name | Yield (%) | Dissolution state (0.5%/50% ethanol) | Color* (ditto) | pH (ditto) | As (312 nm) |
|---|---|---|---|---|---|---|
| 1 | Suei-Ding Hsiang | 2.1 | Partly insoluble | YB | 3.9 | 0.542 |
| 2 | Yui-Jen-Sau | 10.6 | Precipitation | DB | 4.6 | 1.563 |
| 3 | Ban-Ji-Lien | 14.5 | Precipitation | DG | 4.7 | 1.199 |
| 4 | Ban-Bien-Lien | 9.7 | Mostly dissolved | YB | 3.9 | 0.268 |
| 5 | Chi-Mu-Sau | 3.1 | Mostly dissolved | LYB | 4.2 | 1.128 |
| 6 | Ma-Bien-Sau | 9.0 | Precipitation | DB | 4.3 | 0.993 |
| 7 | Tu-Chi-Chi | 16.9 | Partly insoluble | YB | 4.5 | 1.225 |
| 8 | Ma-Ti-Gin | 6.9 | Oily | DB | 4.1 | 0.765 |
| 9 | Yeh-Sia-Chu | 6.9 | Precipitation | DB | 3.8 | 1.604 |
| 10 | Ku-Chi | 6.2 | Precipitation | DB | 4.8 | 0.427 |
| 11 | Bai-Hua-Tsai | 5.0 | Precipitation | DB | 4.2 | 0.567 |
| 12 | San-Jei-Tsai | 4.2 | Oily | DDB | 3.7 | 0.528 |
| 13 | Pien-Di-Gin | 7.0 | Partly insoluble | DB | 4.3 | 1.130 |
| 14 | Sarng-Han-Sau | 5.0 | Oily | YB | 4.8 | 1.536 |
| 15 | Gin-New-Kou | 8.5 | Oily | YE | 4.2 | 0.663 |
| 16 | Mei-Zen-Giau | 1.6 | Mostly dissolved | LYB | 4.3 | 0.550 |
| 17 | Ma-An-Tung | 4.5 | Emulsified | LYB | 4.0 | 1.933 |
| 18 | Hua-Shi-Su | 4.7 | Oily | DG | 4.2 | 0.757 |
| 19 | Gin-Di-Lo | 3.2 | Partly insoluble | BR | 3.9 | 2.101 |
| 20 | Gin-Hsien-Lien | 6.5 | Oily | DG | 4.9 | 0.938 |
| 21 | Nan-Ling-Yia-Hua | 7.6 | Mostly dissolved | LYB | 4.9 | 2.496 |
| 22 | Bai-Yeh-Chi-Ken | 3.9 | Dissolved | RB | 4.5 | 1.145 |
| 23 | Yui-Yeh-Gin-Hua | 3.7 | Mostly dissolved | LY | 4.4 | 1.038 |
| 24 | Hsien-Sau | 3.4 | Partly insoluble | LDG | 5.0 | 0.736 |
| 25 | Taiwan Ma-Dou-Ling | 5.3 | Oily | RB | 3.8 | 0.992 |
| 26 | Shi-Chung-Pu | 7.3 | Oily | YB | 3.8 | 2.494 |
| 27 | Huang-Gin-Guei | 7.0 | Mostly dissolved | RB | 4.9 | 6.078 |
| 28 | Chou-Mor-Li | 3.8 | Mostly dissolved | YE | 4.7 | 0.425 |
| 29 | Da-Ching | 3.8 | Mostly dissolved | YB | 3.8 | 1.209 |
| 30 | Bai-Lorng-Chun-Hua | 5.8 | Mostly dissolved | YE | 4.9 | 0.335 |
| 31 | Mu-Chu-Ma | 2.6 | Mostly dissolved | RB | 4.8 | 0.588 |
| 32 | Ya-Jou | 1.2 | Mostly dissolved | YE | 4.5 | 1.206 |
| 33 | San-Yeh-Pu-Tao | 2.3 | Partly insoluble | YB | 4.6 | 0.879 |
| 34 | Hsia-Yeh-Pu-Tao | 6.8 | Dissolved | RB | 4.3 | 2.739 |
| 35 | Gi-Hua-Mu | 12.6 | Dissolved | LRB | 4.8 | 0.961 |
| 36 | Gin-Shi-Liu | 3.7 | Precipitation | DG | 4.2 | 1.044 |
| 37 | Ha-Sai-Hua | 8.4 | Partly insoluble | BDB | 4.6 | 1.302 |
| 38 | Shi-Sharng-Bor | 2.1 | Partly insoluble | DG | 5.9 | 1.017 |
| 39 | Hu-Ji-Chi | 1.9 | Precipitation | YB | 4.5 | 1.338 |
| 40 | Ci-Yeh-Suei-Ding-Hsiang | 2.4 | Mostly dissolved | YB | 3.7 | 0.618 |
| 41 | Chein-Gin-Tung | 4.9 | Precipitation | BR | 4.0 | 1.030 |
| 42 | Wu-Jei | 4.7 | Precipitation | DG | 7.2 | 0.847 |
| 43 | Tie-Hsien-Jei | 4.3 | Precipitation | YE | 4.0 | 0.700 |
| 44 | San-Hsiang | 1.6 | Precipitation | YE | 4.6 | 0.965 |
| 45 | Gi-Yien-Sau | 5.3 | Oily | DG | 5.1 | 0.910 |
| 46 | Hai-Chou-Chung-San | 2.2 | Dissolved | YE | 5.0 | 1.396 |
| 47 | Huang-Ging | 1.8 | Dissolved | YB | 4.7 | >4.5 |
| 48 | Sarng-Er | 1.9 | Mostly dissolve | LY | 4.3 | 0.257 |
| 49 | Hsien-Fong-Sau | 6.8 | Precipitation | YE | 4.9 | 0.857 |
| 50 | Su-Chi-Sau | 4.4 | Suspended matter | YE | 4.2 | 1.166 |
| 51 | Tsu-Bei-Sau | 2.5 | Precipitation | YE | 4.1 | 0.500 |
| 52 | Harn-Hsiu-Sau | 3.1 | Mostly dissolved | DB | 3.7 | 0.324 |
| 53 | Zu-Chi-Sau | 8.0 | Mostly dissolved | YE | 4.0 | 0.570 |
| 54 | Cher-Chien-Sau | 5.8 | Suspended matter | YE | 3.6 | 0.693 |
| 55 | Dau-Di-Ling | 2.1 | Suspended matter | YE | 4.8 | 0.783 |
| 56 | Bai-Hua-Tung | 4.3 | Mostly dissolved | DB | 3.9 | 0.400 |
| 57 | Ding-Di-Wu-Gong | 2.0 | Precipitation | YE | 6.5 | 2.698 |
| 58 | Da-Gia-Sau | 6.3 | Suspended matter | LY | 4.1 | 0.618 |
| 59 | Gi-Yeh-Tsu-Hua-Di-Ding | 4.6 | Precipitation | OC | 4.8 | 0.700 |
| 60 | Taiwan Her-Shou-Wu | 4.5 | Suspended matter | YB | 4.3 | 0.468 |
| 61 | New-Zu-Zong | 2.9 | Mostly dissolved | LY | 4.5 | 0.436 |
| 62 | Bi-Yeh-Dung-Lorng-Sau | 6.3 | Suspended matter | OC | 4.7 | 0.258 |
| 63 | Karng-Hsiang-Tung | 5.3 | Mostly dissolved | LYB | 4.7 | 1.024 |
| 64 | Taiwan Kou-Tung | 9.0 | Dissolved | DB | 4.6 | 0.418 |

TABLE 2-continued

| No. | Herb name | Yield (%) | Dissolution state (0.5%/50% ethanol) | Color* (ditto) | pH (ditto) | As (312 nm) |
|---|---|---|---|---|---|---|
| 65 | Lo-Chi-Yien-Fu-Mu | 3.4 | Mostly dissolved | YE | 4.2 | 1.314 |
| 66 | Gin-Gien-Sau | 1.5 | Precipitation | YE | 4.6 | 0.506 |
| 67 | Horng-Hua-Su-Wei-Sau | 2.6 | Mostly dissolved | OC | 6.2 | 0.499 |
| 68 | Tu-Chi-Tsai | 4.0 | Precipitation | YE | 4.7 | 0.544 |
| 69 | Dau-Sharng-Sau | 3.6 | Dissolved | LY | 4.7 | 0.379 |
| 70 | Ku-Larn-Parn | 3.7 | Dissolved | YE | 4.5 | 0.445 |
| 71 | Tou-Hua-Hsiang-Ku-Sau | 3.8 | Suspended matter | LY | 4.7 | 0.642 |
| 72 | Du-Horng-Hua | 3.3 | Dissolved | LY | 4.1 | 1.029 |
| 73 | Yeh-Hu | 1.0 | Mostly dissolved | YB | 6.0 | 1.491 |
| 74 | Torng-Chuei-Yui-Di-Sau | 10.5 | Suspended matter | LOC | 4.6 | 0.428 |
| 75 | San-Yeh-Wu-Gia | 5.0 | Suspended matter | LY | 4.5 | 1.445 |

*DG: deep green, LDG: light deep green, OC: olive color, LOC: light olive color, YE: yellow, LY: light yellow, YB: yellowish brown, LYB: light yellowish brown, BR: brown, RB: reddish brown, LRB: light reddish brown, DB: dark brown, DDB: deep dark brown, BDB: blackish dark brown.

TEST EXAMPLE 2

Melanin Formation-inhibiting and Cytotoxic Tests

Measurements were made by the 96-well plate method using Bi 6 mouse melanoma cells (B16-F1 cells, ATCC No. CRL-6323) purchased from Dainippon Pharmaceutical. The cells ($1\times10^4$) were sowed into each well and cultured in 10% FCS- and 1% antibiotic-containing D-MEM for 24 hours (37° C., 5% $CO_2$), the medium was then replaced with D-MEM supplemented with the test substance and theophylline (0.5 mM), and cultivation was further continued for 3 days. The solvent (ethanol) for the test substance was added to the medium in a final concentration of 1%. An equal volume of HEPES buffer (pH 6.8)/ethanol (9:1) was added to the culture supernatant obtained by centrifugation and the absorbance at 475 nm to 660 nm was measured on the microplate reader EL-340 (BIO-TEK INSTRUMENT), and the melanin formation-inhibiting activity was evaluated in terms of the amount of extracellular melanin. The results are shown below in Table 3.

As a result, as is evident from Table 3, 31 herb extracts were found to show an inhibition percentage of 20% or higher at the test concentration of 0.001% and, in particular, 18 items, namely Ku-Chi, Bi-Yeh-Dung-Lorng-Sau, Nan-Ling-Yia-Hua, Shi-Chung-Pu, Ding-Di-Wu-Gong, Yui-Jen-Sau, Sarng-Er, Bai-Hua-Tung, Gi-Hua-Mu, Taiwan Ma-Dou-Ling, Hsien-Fong-Sau, Huang-Gin-Guei, San-Jei-Tsai, Ma-Ti-Gin, New-Zu-Zong, Shi-Sharng-Bor, Horng-Hua-Su-Wei-Sau, Gi-Yeh-Tsu-Hua-Di-Ding, showed an $IC_{50}$ value (i.e., the concentration of the test substance for reducing the amount of extracellular melanin of the controls used) not higher than 10 µg/mL and were found to be more active than arbutin or kojic acid used as the positive controls (Table 3). These active herb extracts were low in toxicity to cells, namely no cytotoxicity was observed at the test concentration of 0.001%.

TABLE 3

| | | Melanin formation inhibition | |
|---|---|---|---|
| No. | Herb name | % Inhibition at 0.001% | $IC_{50}$ µg/mL |
| 10 | Ku-Chi | 104.6 | 1.9 |
| 62 | Bi-Yeh-Dung-Lorng-Sau | 94.3 | 1.9 |
| 21 | Nan-Ling-Yia-Hua | 93.5 | 0.015 |
| 26 | Shi-Chung-Pu | 93.1 | 2.7 |
| 57 | Ding-Di-Wu-Gong | 79.5 | 4.5 |
| 2 | Yui-Jen-Sau | 77.9 | 3.0 |

TABLE 3-continued

| | | Melanin formation inhibition | |
|---|---|---|---|
| No. | Herb name | % Inhibition at 0.001% | $IC_{50}$ µg/mL |
| 48 | Sarng-Er | 72.7 | 3.1 |
| 56 | Bai-Hua-Tung | 70.1 | 3.9 |
| 35 | Gi-Hua-Mu | 67.3 | 4.6 |
| 25 | Taiwan Ma-Dou-Ling | 65.5 | 4.6 |
| 49 | Hsien-Fong-Sau | 64.9 | 3.1 |
| 27 | Huang-Gin-Guei | 64.7 | 3.8 |
| 12 | San-Jei-Tsai | 53.3 | 8.7 |
| 8 | Ma-Ti-Gin | 52.8 | 8.6 |
| 61 | New-Zu-Zong | 51.6 | 7.5 |
| 38 | Shi-Sharng-Bor | 39.4 | 8.8 |
| 67 | Horng-Hua-Su-Wei-Sau | 34.5 | 9.9 |
| 66 | Gin-Gien-Sau | 34.5 | 10.9 |
| 51 | Tsu-Bei-Sau | 29.8 | 10.9 |
| 59 | Gi-Yeh-Tsu-Hua-Di-Ding | 29.1 | 10.0 |
| 15 | Gin-New-Kou | 26.6 | — |
| 29 | Da-Ching | 26.4 | — |
| 11 | Bai-Hua-Tsai | 24.6 | — |
| 39 | Hu-Ji-Chi | 22.7 | — |
| 40 | Ci-Yeh-Suei-Ding-Hsiang | 22.5 | — |
| 13 | Pien-Di-Gin | 22.4 | — |
| 5 | Chi-Mu-Sau | 22.0 | — |
| 20 | Gin-Hsien-Lien | 22.0 | — |
| 16 | Mei-Zen-Giau | 21.9 | — |
| 7 | Tu-Chi-Chi | 21.6 | — |
| 54 | Cher-Chien-Sau | 20.2 | — |
| | Mulberry bark | 61.9 | 3.8 |
| | Arbutin | 32.4 | 12.1 |
| | Kojic acid | 25.7 | 12.9 |

—: not determined

TEST EXAMPLE 3

Elastase Inhibition Test

The synthetic substrate, methoxysuccinyl-Ala-Ala-Ala-Pro-p-nitroanilide (8.0 mM, 25 µL), was reacted with 25 µL of 0.1 M Hepes buffer (pH 7.4, containing 0.5 M NaCl) containing 5 µg/mL human neutrophilic leukocyte-derived elastase and 50 µL of the test sample at 37° C. for 30 minutes and, then, the yield of the decomposition product 4-nitroaniline was determined by measuring the absorbance at 405 nm using the microplate reader EL-340 (Bio-Tek Instrument). The enzyme inhibition rate was calculated using the following formula:

$$\text{Inhibition rate (\%)} = (A-B)/A \times 100$$

where A: absorbance without addition of sample, B: absorbance with addition of sample.

The results are shown below in Table 4.

TABLE 4

| No. | Herb name | Elastase inhibition | |
|---|---|---|---|
| | | % Inhibition at 0.025% | $IC_{50}$ μg/mL |
| 65 | Lo-Chi-Yien-Fu-Mu | 66.6 | 1.4 |
| 34 | Hsia-Yeh-Pu-Tao | 66.5 | 9.0 |
| 52 | Harn-Hsiu-Sau | 63.8 | 46.0 |
| 35 | Gi-Hua-Mu | 61.4 | 10.5 |
| 57 | Ding-Di-Wu-Gong | 60.6 | 54.8 |
| 56 | Bai-Hua-Tung | 58.3 | — |
| 60 | Taiwan Her-Shou-Wu | 56.4 | 63.8 |
| 33 | San-Yeh-Pu-Tao | 56.2 | 22.8 |
| 31 | Mu-Chu-Ma | 52.1 | 50.9 |
| 39 | Hu-Ji-Chi | 49.6 | — |
| 9 | Yeh-Sia-Chu | 35.4 | — |
| 64 | Taiwan Kou-Tung | 34.8 | — |
| 21 | Nan-Ling-Yia-Hua | 34.3 | — |
| 55 | Dau-Di-Ling | 32.0 | — |
| 27 | Huang-Gin-Guei | 30.4 | — |
| 40 | Ci-Yeh-Suei-Ding-Hsiang | 28.6 | — |
| 43 | Tie-Hsien-Jei | 28.4 | — |
| 36 | Gin-Shi-Liu | 24.5 | — |
| | ELHIBIN | 29.3 | |

—: not determined

As shown in Table 4, 18 herb medicines were found to have inhibitory activity of 20% or more at the concentration of 0.025% and, in particular, Lo-Chi-Yien-Fu-Mu, Hsia-Yeh-Pu-Tao, Gi-Hua-Mu, and San-Yeh-Pu-Tao showed a lower $IC_{50}$ value as compared with the positive control substance ELHIBIN (soybean extract, product of PentaPharm) and thus found to have strong elastase-inhibiting activity.

TEST EXAMPLE 4

Hyaluronidase-Inhibiting Test

The sample (100 μL) was added to 50 μL of 0.1 M acetate buffer solution (pH 4.0) containing hyaluronidase (type IV-S from bovine testis, 500 NF units/mL), and the mixture was incubated at 37° C. for 20 minutes. Then, 100 μL of a 0.1 mg/mL solution of the enzyme activator, Compound 48/80, was added, and incubation was further continued at 37° C. for 20 minutes. Thereto was added 250 μL of hyaluronic acid (from rooster comb, 0.5 mg/mL) and after allowing the reaction to proceed at 37° C. for 40 minutes, the reaction was terminated with 100 μL of 0.4 N-NaOH. Then, for assaying N-acetylhexosamine, 120 μL of 0.8 M potassium borate was added to the enzyme reaction mixture, the mixture was heated at 100° C. for 3 minutes and then cooled to room temperature. A 30-μL portion of the mixture was taken out, 180 μL of 1% p-dimethylaminobenzaldehyde in acetic acid was added, and the reaction was allowed to proceed at 37° C. for 20 minutes, After cooling to room temperature, the OD at 590 nm was measured using the microplate reader EL-340 (Bio-Tek Instrument). The inhibition rate (%) was calculated according to the following formula:

Hyaluronidase inhibition rate (%)=$(A-B)/A\times100$ where A: absorbance without addition of sample, B: absorbance with addition of sample.

The results are shown below in Table 5.

TABLE 5

| No. | Herb name | Hyaluronidase inhibition | |
|---|---|---|---|
| | | % Inhibition at 0.02% | $IC_{50}$ μg/mL |
| 34 | Hsia-Yeh-Pu-Tao | 85.9 | 0.0048 |
| 27 | Huang-Gin-Guei | 80.1 | 0.0077 |
| 35 | Gi-Hua-Mu | 41.7 | 0.0122 |
| | Glycyrrhizin | — | 0.0054 |

—: not determined

As a result, when the test was performed at a concentration of 0.02%, an inhibitory activity higher than 40% was observed with three items, namely Hsia-Yeh-Pu-Tao, Huang-Gin-Guei, and Gi-Hua-Mu. Hsia-Yeh-Pu-Tao, in particular, gave a lower $IC_{50}$ value as compared with the positive control substance glycyrrhezin, and thus was found to have strong inhibitory activity.

TEST EXAMPLE 5

SOD-like Activity Test

The test was performed by the 96-well microplate method using the kit "SOD Test Wako" (Wako Pure Chemical Industries) based on the principle of Nitro Blue Tetrazolium (NBT) reduction.

The sample (10 μL) was added to 95 μL of the color reagent solution containing 0.24 M NBT and 0.4 M xanthine. Further, 95 μL of the enzyme solution (xanthine oxidase) was added, and the mixture was incubated at 37° C. for 30 minutes. Thereafter, the enzyme reaction was terminated with 100 μL of the reaction terminating solution (69 mM sodium dodecyl sulfate), and the OD 562 nm was measured on the microplate reader EL-340 (Bio-Tek Instrument). A sample prepared by adding purified water in lieu of the enzyme was used as a blank, and a sample prepared by adding the solvent in lieu of the sample was used as a control. The superoxide anion ($O_{2-}$) elimination rate was calculated by the following formula:

$O_{2-}$ elimination rate (%)=$(A-B)/A\times100$ where A: absorbance of control, B: absorbance with addition of sample.

$IC_{50}$ value represents concentration of test sample at which $O_{2-}$ elimination rate amounts to 50%. The results are shown below in Table 6.

As a result, 57 herb medicines were found to have SOD-like activity (30% or higher) at the concentration of 0.025%. Huang-Gin-Guei, Lo-Chi-Yien-Fu-Mu, and Yeh-Sia-Chu gave a lower $IC_{50}$ value as compared with the positive control substance gambir, and thus were found to have strong SOD-like activity.

TABLE 6

| No. | Herb name | SOD-like activity | |
|---|---|---|---|
| | | % Elimination at 0.025% | $IC_{50}$ μg/mL |
| 27 | Huang-Gin-Guei | 100.8 | 34.5 |
| 35 | Gi-Hua-Mu | 100.2 | 71.6 |
| 65 | Lo-Chi-Yien-Fu-Mu | 99.5 | 53.8 |
| 34 | Hsia-Yeh-Pu-Tao | 95.4 | 77.3 |
| 9 | Yeh-Sia-Chu | 90.9 | 54.5 |
| 22 | Bai-Yeh-Chi-Ken | 79.7 | 82.3 |
| 19 | Gin-Di-Lo | 79.6 | 61.9 |

TABLE 6-continued

| | | SOD-like activity | |
|---|---|---|---|
| No. | Herb name | % Elimination at 0.025% | $IC_{50}$ µg/mL |
| 60 | Taiwan Her-Shou-Wu | 78.2 | 88.3 |
| 32 | Ya-Jou | 74.4 | 86.1 |
| 44 | San-Hsiang | 72.1 | 85.0 |
| 64 | Taiwan Kou-Tung | 70.6 | 90.0 |
| 50 | Su-Chi-Sau | 69.0 | — |
| 36 | Gin-Shi-Liu | 65.3 | — |
| 46 | Hai-Chou-Chung-San | 65.0 | — |
| 58 | Da-Gia-Sau | 61.5 | — |
| 37 | Ha-Sai-Hua | 60.9 | — |
| 31 | Mu-Chu-Ma | 59.7 | — |
| 73 | Yeh-Hu | 59.1 | — |
| 2 | Yui-Jen-Sau | 58.1 | — |
| 29 | Da-Ching | 58 | — |
| 14 | Sarng-Han-Sau | 56.5 | — |
| 6 | Ma-Bien-Sau | 56.2 | — |
| 55 | Dau-Di-Ling | 56.2 | — |
| 69 | Dau-Sharng-Sau | 54.5 | — |
| 26 | Shi-Chung-Pu | 53.0 | — |
| 3 | Ban-Ji-Lien | 52.3 | — |
| 72 | Du-Horng-Hua | 52.3 | — |
| 63 | Karng-Hsiang-Tung | 52.1 | — |
| 53 | Zu-Chi-Sau | 51.4 | — |
| 40 | Ci-Yeh-Suei-Ding-Hsiang | 50.8 | — |
| 71 | Tou-Hua-Hsiang-Ku-Sau | 50.0 | — |
| 18 | Hua-Shi-Su | 49.8 | — |
| 54 | Cher-Chien-Sau | 49.0 | — |
| 66 | Gin-Gien-Sau | 47.3 | — |
| 39 | Hu-Ji-Chi | 47.0 | — |
| 75 | San-Yeh-Wu-Gia | 46.1 | — |
| 24 | Hsien-Sau | 45.3 | — |
| 17 | Ma-An-Tung | 45.2 | — |
| 70 | Ku-Larn-Parn | 43.6 | — |
| 47 | Huang-Ging | 42.8 | — |
| 21 | Nan-Ling-Yia-Hua | 42.6 | — |
| 4 | Ban-Bien-Lien | 41.8 | — |
| 7 | Tu-Chi-Chi | 41.6 | — |
| 74 | Torng-Chuei-Yui-Di-Sau | 41.4 | — |
| 68 | Tu-Chi-Tsai | 41.0 | — |
| 23 | Yui-Yeh-Gin-Hua | 40.9 | — |
| 1 | Suei-Ding Hsiang | 40.0 | — |
| 57 | Ding-Di-Wu-Gong | 39.6 | — |
| 16 | Mei-Zen-Giau | 39.4 | — |
| 41 | Chein-Gin-Tung | 39.2 | — |
| 33 | San-Yeh-Pu-Tao | 37.2 | — |
| 28 | Chou-Mor-Li | 37 | — |
| 11 | Bai-Hua-Tsai | 32.3 | — |
| 52 | Harn-Hsiu-Sau | 31.9 | — |
| 10 | Ku-Chi | 31.2 | — |
| 30 | Bai-Lorng-Chun-Hua | 31.1 | — |
| 43 | Tie-Hsien-Jei | 30.3 | — |
| | Mellisa | — | 50.5 |
| | Gambir | — | 55.0 |

—: not determined

TEST EXAMPLE 6

DPPH Radial-Capturing Activity

| (1) 0.2 M Acetate buffer (pH 5.5) | 50 µL |
|---|---|
| (2) 250 µM DPPH/ethanol | 100 µL |
| (3) Sample/50% ethanol | 100 µL |

(1) to (3) were placed in each well of a 96-well microplate (product of NUNC) and, after 30 minutes of incubation at 30° C., the absorbance at the wavelength 515 nm was measured using the microplate reader EL-340 (BIO-TEK INSTRUMENT). The extent of activity was expressed in terms of DPPH Radial Scavenging (%) calculated according to the following formula:

DPPH Radial Scavenging (%)=$(A-B)/A\times100$ where A: absorbance without addition of sample, B: absorbance with addition of sample.

$IC_{50}$ value=concentration of test compound at which DPPH Radical Scavenging amounts to 50%. The results are shown below in Table 7.

TABLE 7

| | | DPPH radical scavenging | |
|---|---|---|---|
| No. | Herb name | % Inhibition at 0.002% | $IC_{50}$ µg/mL |
| 60 | Taiwan Her-Shou-Wu | 83.5 | 9.3 |
| 65 | Lo-Chi-Yien-Fu-Mu | 82.2 | 8.2 |
| 35 | Gi-Hua-Mu | 77.5 | 2.6 |
| 22 | Bai-Yeh-Chi-Ken | 76.4 | 5.1 |
| 32 | Ya-Jou | 75.7 | 7.2 |
| 9 | Yeh-Sia-Chu | 75.6 | 5.3 |
| 27 | Huang-Gin-Guei | 75.3 | 11.4 |
| 31 | Mu-Chu-Ma | 74.9 | 6.4 |
| 19 | Gin-Di-Lo | 74.5 | 10.4 |
| 36 | Gin-Shi-Liu | 73.2 | 14.6 |
| 64 | Taiwan Kou-Tung | 69.4 | 9.6 |
| 33 | San-Yeh-Pu-Tao | 68.5 | 11.1 |
| 46 | Hai-Chou-Chung-San | 62.8 | 26.0 |
| 2 | Yui-Jen-Sau | 62.3 | 16.5 |
| 29 | Da-Ching | 59.6 | — |
| 37 | Ha-Sai-Hua | 57.8 | — |
| 34 | Hsia-Yeh-Pu-Tao | 57.1 | — |
| 23 | Yui-Yeh-Gin-Hua | 54.4 | — |
| 17 | Ma-An-Tung | 50.5 | — |
| 40 | Ci-Yeh-Suei-Ding-Hsiang | 49.9 | — |
| 1 | Suei-Ding Hsiang | 49.2 | — |
| 63 | Karng-Hsiang-Tung | 45.9 | — |
| 44 | San-Hsiang | 44.2 | — |
| 6 | Ma-Bien-Sau | 42.7 | — |
| 43 | Tie-Hsien-Jei | 38.4 | — |
| 45 | Gi-Yien-Sau | 37.7 | — |
| 24 | Hsien-Sau | 37.6 | — |
| 61 | New-Zu-Zong | 37.2 | — |
| 14 | Sarng-Han-Sau | 36.2 | — |
| 47 | Huang-Ging | 35.5 | — |
| 58 | Da-Gia-Sau | 34.7 | — |
| 57 | Ding-Di-Wu-Gong | 33.8 | — |
| 42 | Wu-Jei | 33.3 | — |
| 39 | Hu-Ji-Chi | 32.4 | — |
| 53 | Zu-Chi-Sau | 32.2 | — |
| 3 | Ban-Ji-Lien | 31.8 | — |
| 21 | Nan-Ling-Yia-Hua | 30.8 | — |
| | Ascorbic acid | — | 4.1 |
| | Glutathione | — | 13.5 |

—: not determined

As a result, 37 herb medicines were found to have 30% or higher DPPH radical scavenging activity at the concentration of 0.002%. In particular, Gi-Hua-Mu gave an $IC_{50}$ value lower than that of the positive control substance ascorbic acid and thus found to have strong DPPH radical capturing activity.

Conclusion: Herb Extracts Having A Plurality of Activities

The medicinal herb extracts from Gi-Hua-Mu and Huang-Gin-Guei were found to have all the above-mentioned activities, namely melanin formation-inhibiting, elastase-inhibiting, hyaluronidase-inhibiting, SOD-like, and DPPH radical-capturing activities. The herb extracts from Nan-Ling-Yia-Hua, Hu-Ji-Chi, Ci-Yeh-Suei-Ding-Hsiang, and Ding-Di-Wu-Gong were found to have melanin formation-inhibiting, eiastase-inhibiting, SOD-like, and DPPH radical-capturing activities simultaneously. The extract from Hsia-Yeh-Pu-Tao was a herb medicine having melanin formation-inhibiting, hyaluronidase-inhibiting, SOD-like and DPPH radical-capturing activities simultaneously. Thus were found a number of herb medicines each having a combination of whitening-antiinflammatory-antioxidant, whitening-antioxidant, whitening-antiinflammatory, or antioxidant-antiinflammatory activities.

The use of such herb medicines having a plurality of activities as medicinal herb extracts to be incorporated into anti-aging compositions can be expected to produce diversified and efficient effects with a smaller number of herb medicines. Further, their effects will be produced synergistically, making it possible to establish formulations with enhanced anti-aging effects.

In the following, typical examples of different preparation forms containing the aging-retarding composition of the invention are described.

ACTUAL EXAMPLE 1

Face Lotions

Face lotions having the respective formulations shown below in Table 8 were prepared by using the extracts of the medicinal herbs Gi-Hua-Mu, Huang-Gin-Guei, Lo-Chi-Yien-Fu-Mu, Hsia-Yeh-Pu-Tao, and Nan-Ling-Yia-Hua.

TABLE 8

| Component | Example No. | | | | |
|---|---|---|---|---|---|
| | 1 | 2 | 3 | 4 | 5 |
| (1) Ethanol | 5.0 | 5.0 | 5.0 | 5.0 | 5.0 |
| (2) 1,3-Butylene glycol | 2.0 | 2.0 | 2.0 | 2.0 | 2.0 |
| (3) Hyaluronic acid | 0.2 | 0.2 | 0.2 | 0.2 | 0.2 |
| (4) Polyoxyethylene hardened castor oil | 0.05 | 0.05 | 0.05 | 0.05 | 0.05 |
| (5) Methyl p-hydroxybenzoate | 0.1 | 0.1 | 0.1 | 0.1 | 0.1 |
| (6) Perfume | 0.1 | 0.1 | 0.1 | 0.1 | 0.1 |
| (7) Gi-Hua-Mu (No. 35) extract | 2.0 | — | — | — | — |
| (7) Huang-Gin-Guei (No. 27) extract | — | 4.0 | — | — | — |
| (7) Lo-Chi-Yien-Fu-Mu (No. 65) extract | — | — | 1.0 | — | — |
| (7) Hsia-Yeh-Pu-Tao (No. 34) extract | — | — | — | 0.02 | — |
| (7) Nan-Ling-Yia-Hua (No. 21) extract | — | — | — | — | 0.01 |
| (8) Distilled water | Rest | Rest | Rest | Rest | Rest |

Preoaration: With respect to each extract (7), components (3) and (7) were dissolved in (8), then components (1), (2), (4), (5) and (7) were added thereto, and the whole was stirred well to obtain each examplified Face lotion.

ACTUAL EXAMPLE 2

Milky Lotions

Milky lotions having the respective formulations shown below in Table 9 were prepared by using the extracts of the medicinal herbs Gi-Hua-Mu, Huang-Gin-Guei Lo-Chi-Yien-Fu-Mu, Hsia-Yeh-Pu-Tao, and Nan-Ling-Yia-Hua.

TABLE 9

| Component | Example No. | | | | |
|---|---|---|---|---|---|
| | 6 | 7 | 8 | 9 | 10 |
| (1) Stearic acid | 2.0 | 2.0 | 2.0 | 2.0 | 2.0 |
| (2) Liquid paraffin | 5.0 | 5.0 | 5.0 | 5.0 | 5.0 |
| (3) squalane | 2.0 | 2.0 | 2.0 | 2.0 | 2.0 |
| (4) Sorbitan monostearate | 1.5 | 1.5 | 1.5 | 1.5 | 1.5 |
| (5) Polyoxyethylene(20)-sorbitan monostearate | 2.0 | 2.0 | 2.0 | 2.0 | 2.0 |

TABLE 9-continued

| Component | Example No. | | | | |
|---|---|---|---|---|---|
| | 6 | 7 | 8 | 9 | 10 |
| (6) Butyl p-hydroxybenzoate | 0.05 | 0.05 | 0.05 | 0.05 | 0.05 |
| (7) Glycerol | 2.0 | 2.0 | 2.0 | 2.0 | 2.0 |
| (8) Methyl p-hydroxybenzoate | 0.1 | 0.1 | 0.1 | 0.1 | 0.1 |
| (9) Perfume | 0.15 | 0.15 | 0.15 | 0.15 | 0.15 |
| (10) Gi-Hua-Mu (No. 35) extract | 5.0 | — | — | — | — |
| (10) Huang-Gin-Guei (No. 27) extract | — | 5.0 | — | — | — |
| (10) Lo-Chi-Yien-Fu-Mu (No. 65) extract | — | — | 1.0 | — | — |
| (10) Hsia-Yeh-Pu-Tao (No. 34) extract | — | — | — | 0.2 | — |
| (10) Nan-Ling-Yia-Hua (No. 21) extract | — | — | — | — | 0.1 |
| (11) Distilled water | Rest | Rest | Rest | Rest | Rest |

Preparation: With respect to each extract (10), components (7) (8) and (10) were added to (11), then components (1) to (6) were added thereto at 80° C. and, after thorough emulsification, component (9) was added, and the whole was cooled to room temperature, to obtain each examplified Milky lotion.

ACTUAL EXAMPLE 3

Creams

Creams having the respective formulations shown below in Table 10 were prepared by using the extracts of the medicinal herbs Gi-Hua-Mu, Huang-Gin-Guei, Lo-Chi-Yien-Fu-Mu, Hsia-Yeh-Pu-Tao, and Nan-Ling-Yia-Hua.

TABLE 10

| Component | Example No. | | | | |
|---|---|---|---|---|---|
| | 11 | 12 | 13 | 14 | 15 |
| (1) Liquid paraffin | 23.0 | 23.0 | 23.0 | 23.0 | 23.0 |
| (2) Vaseline | 7.0 | 7.0 | 7.0 | 7.0 | 7.0 |
| (3) Cetanol | 1.0 | 1.0 | 1.0 | 1.0 | 1.0 |
| (4) Stearic acid | 2.0 | 2.0 | 2.0 | 2.0 | 2.0 |
| (5) Beeswax | 2.0 | 2.0 | 2.0 | 2.0 | 2.0 |
| (6) Sorbitan monostearate | 3.5 | 3.5 | 3.5 | 3.5 | 3.5 |
| (7) Polyoxyethylene(20)-sorbitan monostearate | 2.5 | 2.5 | 2.5 | 2.5 | 2.5 |
| (8) Butyl p-hydroxybenzoate | 0.05 | 0.05 | 0.05 | 0.05 | 0.05 |
| (9) Hyaluronic acid | 0.1 | 0.1 | 0.1 | 0.1 | 0.1 |
| (10) 1,3-Butylene glycol | 1.0 | 1.0 | 1.0 | 1.0 | 1.0 |
| (11) Methyl p-hydroxy-benzoate | 0.1 | 0.1 | 0.1 | 0.1 | 0.1 |
| (12) Perfume | 0.15 | 0.15 | 0.15 | 0.15 | 0.15 |
| (13) Lactobacillus culture fluid | 5.0 | 5.0 | 5.0 | 5.0 | 5.0 |
| (14) Gi-Hua-Mu (No. 35) extract | 0.2 | — | — | — | — |
| (14) Huang-Gin-Guei (No. 27) extract | — | 0.5 | — | — | — |
| (14) Lo-Chi-Yien-Fu-Mu (No. 65) extract | — | — | 0.25 | — | — |
| (14) Hsia-Yeh-Pu-Tao (No. 34) extract | — | — | — | 0.1 | — |
| (14) Nan-Ling-Yia-Hua (No. 21) extract | — | — | — | — | 0.05 |
| (16) Distilled water | Rest | Rest | Rest | Rest | Rest |

Preparation: With respect to each extract (14), components (10) (11), (13) and (14) were added to (15), and component (9) was dispersed therein. To the dispersion were added components (1) to (8) at 80° C. for emulsifying them, component (12) was then added, and the whole was cooled, to obtain each examplified Cream.

The basal cosmetics obtained in Example Nos. 1 to 15 as obtained according to the respective formulations as mentioned above had good melanin formation-inhibiting, elastase-inhibiting, hyaluronidase-inhibiting, SOD-like, and/or DPPH radical-scavenging activities. These basal cosmetics can produce good effects in reducing the color of or whitening post-sunburn pigmentation, blotches, freckles, liver spots and so forth and, further, they are effective in restoring and/or maintaining the tension and elasticity of the skin through their elastase-inhibiting activity and, thus, in preventing or retarding skin aging and maintaining the fresh condition of the skin.

The skin age-retarding composition according to the present invention have antioxidant activity as well. Thus, cosmetics and other compositions excellent in safety and stable against oxidation can be produced by appropriately using them. Such compositions are effective in preventing sebum components of the skin from being oxidized and against oxidative skin damages and skin aging and, thus, they can protect the skin. The compositions according to the present invention are medicinal herb extract-containing ones and, when externally applied to the human skin, they give good feel and touch. They are thus very useful in beauty treatment and medical treatment.

The medicinal herb extracts used in the present invention have whitening, antiinflammatory and antioxidant activities. While the extracts each independently has strong activity, some have a plurality of activities in combination. They are useful as age-retarding materials for use in dermatologic preparations. Th y are highly safe and can be used continuously for a long period of time.

As described her inabove, the present invention has an industrial applicability for advantageously providing skin age-retarding compositions which have whitening activity, maintain the tension and elasticity of the skin, increase the retention of moisture in the skin and, further, have antiinflammatory/antiallergic activity.

What is claimed is:

1. A method for retarding skin aging comprising applying to the skin of a human a pharmaceutically effective amount of a composition which comprises a base and/or one or more additives medicinally acceptable for external dermal application and a pharmaceutically effective amount of one or more plant extracts having an active oxygen eliminating or scavenging activity which provides an age-retardin effect, said active oxygen eliminating or scavenging activity evaluated by an $O_{2-}$ elimination rate of $((A-B)/A) \times 100$ being more than 30%, wherein A denotes the absorbance of a control, B denotes the absorbance with the addition of a sample, wherein the OD at 562 nm is measured after incubating a color reagent solution containing Nitro Blue Tetrazolium and xanthine, xanthine oxidase and the plant extract at a concentration of 0.025% at 37° C. for 30 minutes, the plant extract being selected from the group consisting of extracts of Suei-Ding Hsiang (*Ludwigia octovalvis*), Yui-Jen-Sau (*Anisomeles indica*), Ban-Ji-Lien (*Scutellaria rivularis*), Ma-Bien-Sau (*Verbana officinalis*), Ku-Chi (*Physalis angulata*), Bai-Hua-Tsai (*Cleome gynandra*), Sarng-Han-Sau (*Vernonia cinerae*), Ma-An-Tung (*Ipomoea pes-caprae*), Hua-Shi-Su (*Clerodendrum calamitosum*), Gin-Di-Lo (*Drosera burmanni*), Bai-Yeh-Chi-Ken (*Elaeagnus oldhamii*), Yui-Yeh-Gin-Hua (*Mussaenda parviflora*), Chou-Mor-Li (*Clerodendrum philippinum*), Da-Ching (*Clerodendrum crytophyllum*), Bai-Lorng-Chun-Hua (*Clerodendrum paniculataum* var. *albifloraum*), Mu-Chu-Ma (*Boehmeria densiflora*), Ya-Jou (*Sapium sebiferum*), San-Yeh-Pu-Tao (*Tetrastigma dentatum*), Gin-Shi-Liu (*Bredia oldhami*), Ha-Sai-Hua (*Staurogyne concinnula*), Ci-Yen-Suei-Ding-Hsiang (*Ludwigia hyssopifolia*), Tie-Hsien-Jei (*Adiantum flabellulatum*), Huang-Ging (*Vitix negundo*), Su-Chi-Sau (*Gnaphalium affine*), Zu-Chi-Sau (*Euphorbia hirta*), Ding-Di-Wu-Gong (*Torenia concolor* var. *formosana*), Da-Gia-Sau (*Euphorbia formosana*), Taiwan Kou-Tung (*Uncaria hirsuta*), Cher-Chien-Sau (*Plantago formosana*), Gin-Gien-Sau (*Rubia lanceolata*), Tu-Chi-Tsai (*Ixeris chinensis*), Dau-Sharng-Sau (*Ixeris laevigata* var. *oldhami*), Ku-Lam-Parn (*Clerodendrum inerme*), Du-Horng-Hua (*Callicarpa formosana*), Torng-Chuei-Yui-Di-Sau (*Pratia nummularia*) and San-Yeh-Wu-Gia (*Acanthopanax trifoliatus*).

2. A method for retarding skin aging comprising applying to the skin of a human a pharmaceutically effective amount of a composition which comprises a base and/or one or more additives medicinally acceptable for external dermal application and a pharmaceutically effective amount of one or more plant extracts having an antioxidant activity which provides an age-retarding effect, said antioxidant activity being evaluated by a DPPH radical scavenging of $((A \times B)/A) \times 100$ being more than 30%, wherein A denotes the absorbance without the addition of a sample, B denotes the absorbance with the addition of a sample, wherein the absorbance of 515 nm is measured after incubating a mixture consisting of 50 µL of 0.2 M acetate buffer (pH of 5.5), 100 µL of 250 µM DPPH/ethanol and 100 µL of sample/50% ethanol for 30 minutes at 30° C., the plant extract being selected from the group consisting of extracts of Suei-Ding-Hsiang (*Ludwigia octovalvis*), Yui-Jen-Sau (*Anisomeles indica*), Ban-Ji-Lien (*Scutellaria rivularis*), Ma-Bien-Sau (*Verbana officinalis*), Sarng-Han-Sau (*Vermonia cinerae*), Ma-An-Tung (*Ipomoea pes-caprae*), Gin-Di-Lo (*Drosera burmanni*), Bai-Yeh-Chi-Ken (*Elaeagnus oldhamii*), Yui-Yeh-Gin-Hua (*Mussaenda parviflora*), Da-Ching (*Clerodendrum cyrtophyllum*), Mu-Chu-Ma (*Boehmeria densiflora*), Ya-Jou (*Sapium sebiferum*), San-Yeh-Pu-Tao (*Tetrastigma dentatum*), Gin-Shi-Liu (*Bredia oldhami*), Ha-Sai-Hua (*Staurogyne concinnula*), Ci-Yeh-Suei-Ding-Hsiang (*Ludwigia hyssopifolia*), Wu-Jei (*Sphenomeris chusana*), Tie-Hsien-Jei (*Adiantum flabellulatum*), Gi-Yien-Sau (*Kummerowia striata*), Huang-Ging (*Vitex negundo*), Zu-Chi-Sau (*Eurohorbia hirta*), Ding-Di-Wu-Gong (*Torenia concolor* var. *formosana*), Da-Gia-Sau (*Euphorbia formosana*), New-Zu-Zong (*Ficus erecta* var. *beecheyana*) and Taiwan Kou-Tung (*Uncaria hirsuta*).

3. A composition for retarding skin aging comprising a base and/or one or more additives medicinally acceptable for external dermal application and a pharmaceutically effective amount of one or more plant extracts having an elastase-inhibiting activity to provide an age retarding effect, said elastase-inhibiting activity evaluated by an inhibition rate of $((A-B)/A) \times 100$ being higher than 20%, where A denotes the absorbance without the addition of a sample and B denotes the absorbance with the addition of a sample, wherein the absorbance at 405 nm is measured after reacting a synthetic substrate, an elastase component buffer solution and the plant extract at a concentration of 0.025% at 37° C. for 30 minutes, and wherein the plant extract is San-Yeh-Pu-Tao (*Tetrastigma dentatum*).

\* \* \* \* \*